United States Patent [19]

Hofmann

[11] Patent Number: 5,176,674
[45] Date of Patent: Jan. 5, 1993

[54] ANGIOPLASTY LIGHT GUIDE CATHETER FOR THE REMOVAL OF STENOSES USING LASER LIGHT ENERGY

[75] Inventor: Eugen Hofmann, Zurich, Switzerland

[73] Assignee: Schneider (Europe) AG, Zurich, Switzerland

[21] Appl. No.: 656,933

[22] Filed: Feb. 15, 1991

[30] Foreign Application Priority Data

Mar. 5, 1990 [CH] Switzerland ............... 00690/90

[51] Int. Cl.⁵ ................................. A61B 17/36
[52] U.S. Cl. ........................... 606/7; 606/15
[58] Field of Search ............. 606/7, 15, 194, 2, 10, 606/11, 12, 13, 14, 16, 17, 193; 604/19, 21; 128/6, 634, 395–398

[56] References Cited

U.S. PATENT DOCUMENTS

| 4,228,801 | 10/1980 | Magnasco et al. | 606/193 |
| 4,966,596 | 10/1990 | Kuntz et al. | 606/7 |
| 4,993,412 | 2/1991 | Murphy-Chutorian | 606/7 |
| 5,041,089 | 8/1991 | Mueller et al. | 606/7 X |
| 5,041,108 | 8/1991 | Fox et al. | 606/7 |
| 5,066,292 | 11/1991 | Müller et al. | 606/7 |

Primary Examiner—Peter A. Aschenbrenner
Attorney, Agent, or Firm—Peter C. Richardson; Lawrence C. Akers; John L. LaPierre

[57] ABSTRACT

An angioplasty balloon catheter wherein the balloon thereof has connected to its wall a plurality of laser light guides which are inlaid in the balloon wall so that the distal ends of the light guides can be moved radially outwardly and inwardly by changing pressure within the balloon.

7 Claims, 2 Drawing Sheets

FIG. 3
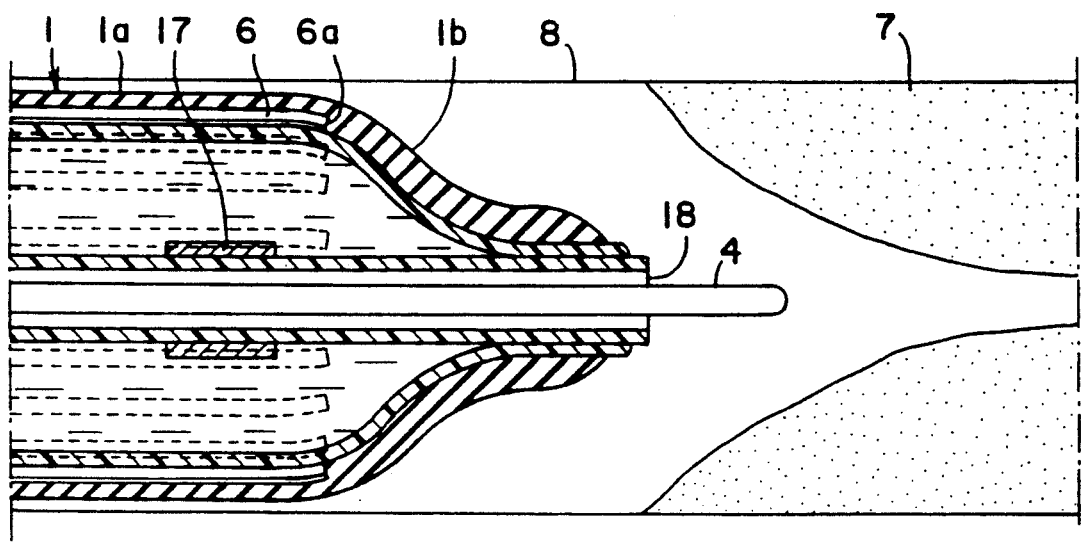
FIG. 4
FIG. 5
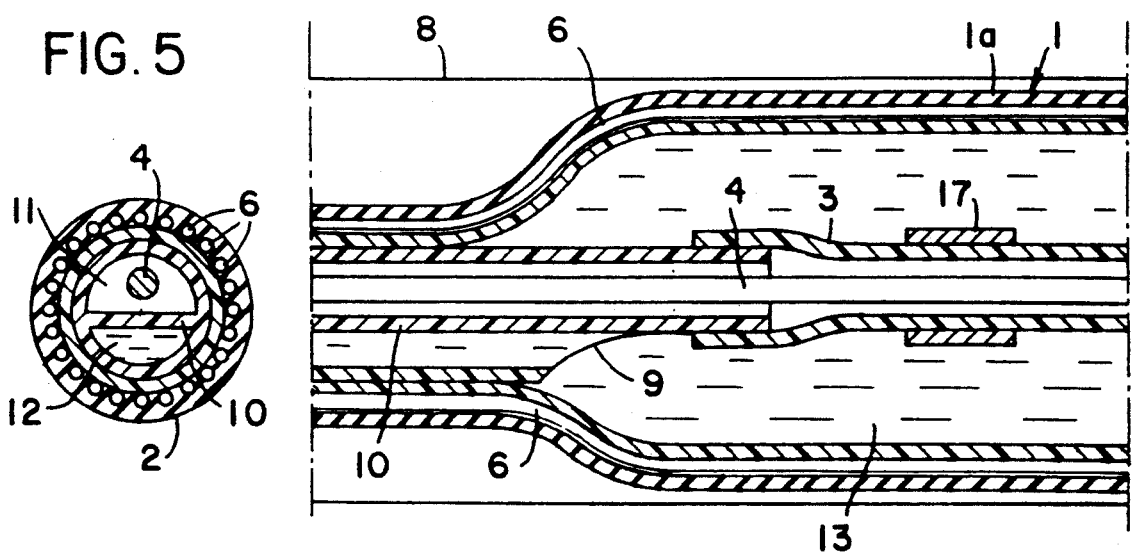

ANGIOPLASTY LIGHT GUIDE CATHETER FOR THE REMOVAL OF STENOSES USING LASER LIGHT ENERGY

BACKGROUND OF THE INVENTION

The invention relates to an angioplasty light guide catheter.

The use of laser beams for the treatment of stenoses was proposed more than 25 years ago. Although this method too, in addition to the known balloon dilatation, permits treatment without surgical intervention and from the start was very promising, the opening of stenosed vessels using laser light has nevertheless scarcely progressed beyond the experimental stage. An important reason for this is that no suitable catheter was available which permitted an accurate positioning of the light guides in the vessel. Nor has a solution hitherto been found to the risk of dissection of the vessel wall.

An angioplasty light guide catheter is known in which the laser light is bundled with lenses. An angioplasty light guide catheter is also known from an article in the periodical Herz+Gefass 5 (1985) page 185, FIG. 5, in which three concentrically arranged laser light guides can be held in the vessel stable against the wall by means of a balloon. In this catheter too, an accurate positioning and control of the laser light is not possible, and the risk of dissection is relatively high. In this case there is also the disadvantage that, with a catheter with a wall-stable laser light guide, severe occlusions cannot be treated successfully. In the case of such severe occlusions, a catheter with a centrally arranged light guide, as is known from the periodical JACC Volume 8 (5), November 1986; 1989-95 (FIG. 1), would be better suited.

SUMMARY OF THE INVENTION

The object of the invention is to provide a catheter of the said generic type, with which the laser light can be controlled safely and simply, and which is suitable for the treatment of stenoses of varying degrees, without any risk of dissection of the vessel wall.

In the catheter according to the invention, the distance of the exit points of the light guides from the centre line of the balloon is a function of the pressure of the balloon fluid. This pressure can be altered and controlled accurately and in a simple manner by the surgeon. In the case of a low pressure and a correspondingly small diameter of the dilatation balloon, the laser light is concentrated in the vessel centre and is therefore particularly suitable for the treatment of severe stenoses. In the case of a higher pressure, the exit points lie correspondingly closer to the inside wall of the vessel, and the outer-lying areas of stenoses can also be removed correspondingly. Further advantageous features will emerge from the dependent claims and from the description.

BRIEF DESCRIPTION OF THE DRAWINGS

An exemplary embodiment of the invention is illustrated in greater detail below with reference to the drawings, in which:

FIG. 3 shows a longitudinal section through the distal end of a dilated balloon in a diagrammatically represented stenosed vessel section, FIG. 4 shows a longitudinal section through the rear area of a dilatation balloon, and FIG. 5 shows a cross-section through the shaft of a catheter according to the invention.

DETAILED DESCRIPTION OF A PREFERRED EMBODIMENT

Figure 1:
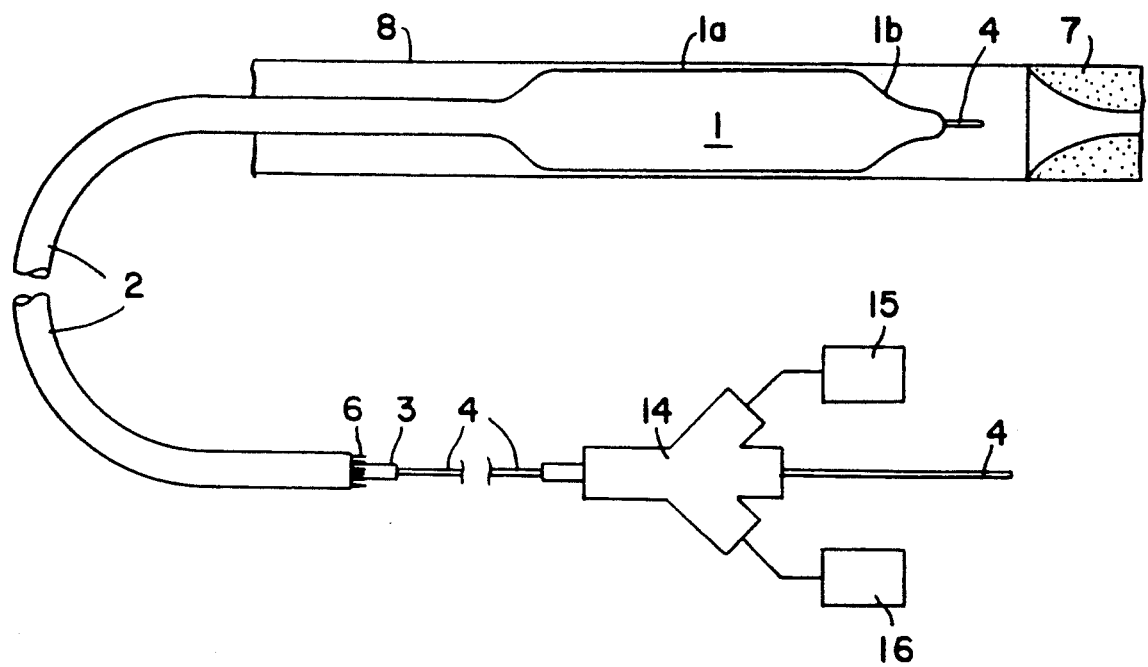
FIG. 1 shows diagrammatically a stenosed vessel section with the dilatation balloon inserted.

FIG. 1 shows, purely diagrammatically, a blood vessel 8 with a stenosis 7, and a catheter with a dilatation balloon 1 and a catheter shaft 2 inserted percutaneously into the vessel. The catheter is inserted into the vessel 8 using a guide wire 4. The guide wire 4 extends through the shaft 2 and the dilatation balloon 1 and can emerge at a distal opening 18. As FIG. 5 shows, the shaft 2 is divided by a wall 10 into a lumen 11 for the guide wire 4 and a lumen 12 for pressure fluid. The lumen 12 is connected, according to FIG. 4, via an opening 9 to the balloon interior 13, and connected at the proximal end to a suction and pressure pump 16. By means of the pump 16, the pressure in the interior 13 of the dilatation balloon 1 can be regulated accurately and, consequently, the diameter of the balloon can be regulated. When the catheter is introduced, the dilatation balloon 1 is folded in a known manner. In the unfolded state, the dilatation balloon 1, as can be seen from FIG. 1, is externally cylindrical between the two tapering ends.

Figure 2:
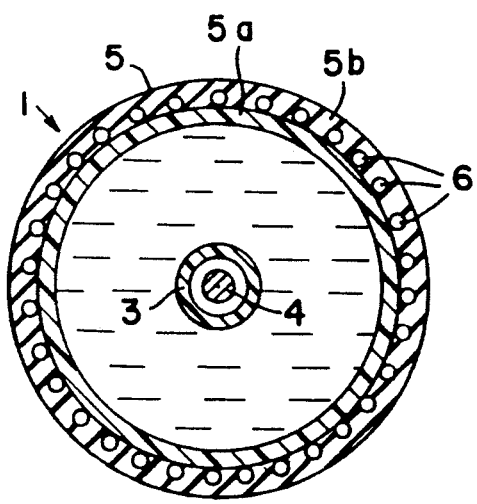
FIG. 2 shows a cross-section through a dilatation balloon.

According to FIG. 2, the wall 5 of the dilatation balloon 1 consists of an inner layer 5a and an outer layer 5b. The inner layer 5a consists of a relatively soft plastic and the outer layer 5b preferably of silicone rubber. In contrast to the known dilatation balloons, the wall 5 of the dilatation balloon 1 is elastically extensible within certain limits. Light guide fibres or bundles 6 are stuck onto the inner layer 5a and are covered by the outer layer 5b to thereby be embedded in the outer layer. These light guides 6 are distributed uniformly over the periphery of the wall 5 and run parallel to the longitudinal direction of the catheter 6. When the balloon 1 is dilated, the exit points 6a of the light guides 6 lie in a circle and in a plane which intersects the dilatation balloon approximately at the transition between its cylindrical area 1a and its distal tapered area 1b. The light guides 6 also extend over the entire length of the shaft 2 and are coupled via a connection piece 14 to a laser device 15. The device 15 is preferably a pulsating xenon-chloride excimer laser. The light generated by the laser device 15 passes via the connection piece 14 and the shaft 2 to the exit points 6a of the light guides 6.

The light guides 6 have a diameter of for example 0.1 mm and are very flexible. The dilatation balloon 1 can thus be folded even with the light guides 6 inserted. The radial distance of the light guides 6 from the centre line of the dilatation balloon 1 increases as the pressure of the fluid present in the balloon increases. Accordingly, the distance of the exit points 6a from the centre line of the dilatation balloon 1 is a function of the pressure which can be regulated by the pump 16. Since the wall 5 is elastically extensible, it is possible, by means of the pressure regulation, to arrange the exit points 6a in circles of differing radii. Accordingly, the laser beams emerging at the exit points 6a strike the stenosis 7 at a greater or lesser distance from the inner side of the vessel. When the pressure in the dilatation balloon is relatively low, a correspondingly intense laser light bundle is thus directed towards the centre of the stenosis. In contrast, in the case of a higher pressure, the more outer areas of the stenosis 7 are removed with less dense laser light.

As shown in FIG. 3, the dilatation balloon 1 is positioned in front of the stenosis 7 for the removal of the stenosis 7 using laser light. The position of the dilatation catheter 1 can be observed using a marker strip 17. In addition to the removal of the stenosis using laser light energy, the use of conventional balloon dilatation is also conceivable with the catheter according to the invention. Thus, without changing the catheter, a stenosis 7 can be expanded with the dilatation balloon 1 before or after treatment using laser light energy.

I claim:

1. Angioplasty light guide catheter for the removal of stenoses using laser light energy, with a dilatation balloon to be introduced percutaneously into the vessel to be treated and with several light guides which end in the area of the dilatation balloon for emission and at the proximal end of a shaft of the catheter for admission of the laser light, characterized in that the light guides have, at least in the area of the dilatation balloon, a diameter which is not substantially greater than the thickness of the wall of the dilatation balloon and are connected to the wall and in particular inlaid in the latter in such a way that, at their distal ends, they can be moved radially outwards and inwards by means of pressure changes in the dilatation balloon while remaining substantially parallel with the longitudinal axis of the catheter.

2. Catheter according to claim 1, characterized in that the light guides are flexible phases with a diameter smaller than about 0.5 mm.

3. Catheter according to claim 1, characterized in that the light guides are embedded in the wall of the dilatation balloon.

4. Catheter according to claim 1, characterized in that the wall has an inner layer on which an outer layer is applied, and in that the light guides are embedded in the outer layer.

5. Catheter according to claim 4, characterized in that the outer layer is made of silicone rubber.

6. Catheter according to one of claim 1, characterized in that the wall of the dilatation balloon is made of relatively soft and flexible plastic material.

7. Catheter according to claim 1, characterized in that it is connected to a pulsating xenon-chloride excimer laser.

* * * * *